United States Patent
Chen et al.

(10) Patent No.: US 11,198,892 B2
(45) Date of Patent: Dec. 14, 2021

(54) **METHOD OF PRODUCING OIL CONTAINING POLYUNSATURATED FATTY ACIDS BY USING *SCHIZOCHYTRIUM* SP**

(71) Applicant: INFINITUS (CHINA) COMPANY LTD., Guangdong (CN)

(72) Inventors: Zehua Chen, Guangdong (CN); Yong Zhou, Guangdong (CN); Jian Tang, Guangdong (CN); Yonghua Wang, Guangdong (CN); Zheng Xiao, Guangdong (CN); Chenfeng Jing, Guangdong (CN); Dong Liang, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 0 days.

(21) Appl. No.: 16/878,612

(22) Filed: May 20, 2020

(65) Prior Publication Data
US 2020/0370078 A1 Nov. 26, 2020

(30) Foreign Application Priority Data
May 20, 2019 (CN) .......................... 201910418891.5

(51) Int. Cl.
*C12P 7/64* (2006.01)
*C12N 1/12* (2006.01)

(52) U.S. Cl.
CPC .............. *C12P 7/6427* (2013.01); *C12N 1/12* (2013.01); *C12N 2500/05* (2013.01); *C12N 2500/32* (2013.01); *C12N 2500/34* (2013.01)

(58) Field of Classification Search
CPC ... C11B 3/003; C11B 1/10; C11B 3/02; C11B 3/16; C12N 9/18; C12N 1/12; C12N 1/06; C12N 1/22; C12N 2500/05; C12N 2500/32; C12N 2500/34; C12P 7/6427; C12P 19/02; C12P 19/14; C12P 1/00; C12P 21/02; C12P 2203/00; C12P 23/00; C12P 39/00; C12P 7/04; C12P 7/065; C12P 7/6409; C12P 7/6472; B01D 15/00; B01D 15/1807; B01D 15/1871; B01J 20/20; B01J 20/28026; B01J 20/3416; B01J 20/3475; B01J 2220/62; C08H 8/00; Y02E 50/10; Y02E 50/17; Y02E 50/16
See application file for complete search history.

(56) References Cited

U.S. PATENT DOCUMENTS

| | | | |
|---|---|---|---|
| 5,130,242 A * | 7/1992 | Barclay ................... | A61K 31/20 435/134 |
| 8,389,808 B2 * | 3/2013 | Damude ................ | A23K 50/80 800/298 |
| 8,722,384 B2 * | 5/2014 | Knutzon .............. | A23K 20/158 435/252.3 |
| 8,809,026 B2 * | 8/2014 | Vanhercke ........... | C07K 14/415 435/134 |
| 9,127,288 B2 * | 9/2015 | Petrie .................... | C12N 9/1029 |
| 9,499,829 B2 * | 11/2016 | Vanhercke ................ | C11B 3/10 |
| 10,246,718 B2 * | 4/2019 | Vanhercke .............. | C10L 1/026 |
| 10,323,209 B2 * | 6/2019 | Wood ....................... | A23D 9/00 |
| 10,385,289 B2 * | 8/2019 | Cherinko ................. | C11B 3/02 |
| 10,392,578 B2 * | 8/2019 | Cherinko ................. | C11B 3/02 |
| 10,472,587 B2 * | 11/2019 | Vanhercke .............. | C10L 1/026 |
| 10,925,293 B2 * | 2/2021 | Petrie .................... | C12N 9/1025 |
| 2010/0310710 A1 * | 12/2010 | Knutzon ................. | A23L 33/40 426/2 |
| 2011/0256260 A2 * | 10/2011 | Knutzon .............. | A23K 20/158 426/2 |
| 2011/0295028 A1 * | 12/2011 | Cherinko ................... | C11B 3/16 554/175 |
| 2011/0314725 A1 * | 12/2011 | Petrie ....................... | A23D 9/00 44/388 |
| 2013/0247451 A1 * | 9/2013 | Vanhercke .............. | C10L 1/026 44/388 |
| 2014/0323569 A1 * | 10/2014 | Raman ................ | C12R 2001/89 514/547 |
| 2017/0029731 A1 * | 2/2017 | Vanhercke ............... | C10G 2/00 |
| 2018/0066288 A1 * | 3/2018 | Nolasco .................... | C12P 1/00 |
| 2018/0142183 A1 * | 5/2018 | Cherinko ................. | C11B 1/10 |
| 2019/0203125 A1 * | 7/2019 | Vanhercke ................ | C01B 3/22 |
| 2019/0300894 A1 * | 10/2019 | Vanhercke ............. | A23K 10/30 |
| 2019/0338214 A1 * | 11/2019 | Cherinko ................. | C11B 1/10 |

* cited by examiner

*Primary Examiner* — Deborah K Ware
(74) *Attorney, Agent, or Firm* — Yue (Robert) Xu; Apex Attorneys at Law, LLP

(57) ABSTRACT

Provided is a method of producing an oil containing polyunsaturated fatty acids by using *Schizochytrium* sp. The method comprises: performing fermentation using *Schizochytrium* sp.; resuspending the resultant cells after fermentation in water, adding cellulase and neutral protease for enzymolysis; mixing the enzymatic hydrolyzate with n-hexane, shaking, extracting, centrifuging, and collecting the n-hexane phase; concentrating the n-hexane phase under reduced pressure to remove the n-hexane, and drying to obtain an oil; performing a first crystallization and a second crystallization, and then performing cold filtration to obtain a liquid oil after the second crystallization; and subjecting the liquid oil to deacidification and decolorization. By regulating fermentation conditions and conducting concentration processing on polyunsaturated fatty acids, the content of eicosapentaenoic acid in the *Schizochytrium* sp. is increased to more than 12%, and the obtained oil is rich in docosahexaenoic acid, docosapentaenoic acid and eicosapentaenoic acid.

10 Claims, No Drawings

METHOD OF PRODUCING OIL CONTAINING POLYUNSATURATED FATTY ACIDS BY USING *SCHIZOCHYTRIUM* SP

CROSS REFERENCE TO RELATED APPLICATIONS

This application claims the priority of Chinese Patent Application No. 201910418891.5, filed on May 20, 2019, and the disclosures of which are hereby incorporated by reference.

FIELD OF THE INVENTION

The invention relates to the field of microbial oils, in particular to a method of producing an oil containing polyunsaturated fatty acids by using *Schizochytrium* sp.

BACKGROUND OF THE INVENTION

Currently, commercial omega-3 polyunsaturated fatty acids (PUFAs) are mainly derived from marine fishes. Fish oils as a source are severely affected by fishy odor and stability, which limit its use as a food additive and food supplement. Global fish resources have tended to decrease due to overfishing, and the increasingly scarce seafood fish oils are difficult to meet the growing demand of people for eicosapentaenoic acid (EPA) and docosahexaenoic acid (DHA). In addition, the supply and the quality of fish oils are greatly affected by season and weather changes, and marine pollution caused by toxic impurities of heavy metals and organics has also limited the further development of PUFAs derived from fish oils. The high market price of omega-3 PUFAs makes many potential applications of fish oils difficult to achieve. Realizing that the supply of ω-3 PUFAs will lag far behind the demand thereof, people began to seek new sources of ω-3 PUFAs.

PUFAs products from fish oil usually have the contents of DHA and EPA above 10%, which is a composite PUFAs product with multiple physiological activities and functions that are difficult to achieve with single PUFA. However, the contents of DHA and EPA in an oil fermented by single microalgae in the literatures cannot reach this level at the same time. *Schizochytrium* sp. is one of the most studied heterotrophic microalgae for DHA production, which is a very promising alternative resource for omega-3 PUFAs production. It has low production cost, fast fermentation, high biomass, high oil yield, and high strain safety, which is a national-approved algae oil production strain.

At present, under ordinary fermentation conditions, the DHA content in the oil of *Schizochytrium* sp. reaches more than 35%, while the EPA content is only about 0.5-1.0%. The EPA content is far lower than that in fish oils, making it difficult to develop composite PUFAs products.

SUMMARY OF THE INVENTION

In view of this, the present invention provides a method of producing an oil containing polyunsaturated fatty acids by using *Schizochytrium* sp. The invention successfully achieves that by regulating fermentation conditions and conducting concentration processing on polyunsaturated fatty acids, the content of eicosapentaenoic acid in the *Schizochytrium* sp. is increased to more than 12%, and the produced oil is rich in docosahexaenoic acid, docosapentaenoic acid and eicosapentaenoic acid. The invention provides a novel oil product which can be used to replace the polyunsaturated fatty acids from fish oils, showing a significant industrial development value.

In order to achieve the above-mentioned objects, the present invention provides the following technical solutions.

The present invention provides a method of producing an oil containing polyunsaturated fatty acids by using *Schizochytrium* sp., comprising the following steps:

Step (1): performing fermentation using *Schizochytrium* sp., wherein the medium for fermentation comprises glucose 90-120 g/L, sodium glutamate 16-32 g/L, yeast powder 2-16 g/L, magnesium sulfate 1.8-3.24 g/L, ammonium sulfate 3.5-6.8 g/L, potassium chloride 0.5-1.5 g/L, potassium dihydrogen phosphate 3.2-3.8 g/L, sodium sulfate 35-45 g/L, and water as balance;

Step (2): resuspending the resultant cells after fermentation in water, adding cellulase and neutral protease for enzymolysis to obtain an enzymatic hydrolyzate;

Step (3): mixing the enzymatic hydrolyzate with n-hexane, shaking, extracting, centrifuging, and collecting the n-hexane phase; concentrating the n-hexane phase under reduced pressure to remove the n-hexane, and drying to obtain an oil;

Step (4): performing a first crystallization on the oil, then performing cold filtration to obtain a solid oil and a liquid oil;

Step (5): performing a second crystallization on the liquid oil, then performing cold filtration to obtain a liquid oil after the second crystallization;

Step (6): subjecting the liquid oil after the second crystallization to deacidification and decolorization.

Preferably, the medium for fermentation comprises: glucose 100 g/L, sodium glutamate 20 g/L, yeast powder 4 g/L, magnesium sulfate 2.24 g/L, ammonium sulfate 4.8 g/L, potassium chloride 1 g/L, potassium dihydrogen phosphate 3.5 g/L, sodium sulfate 37 g/L, and the balance of water.

As a preference, the fermentation is performed at conditions: an inoculum size of 5-15%, a shaking speed of 200-500 rpm, an air flow of 0.5-2 vvm, a temperature of 23-29° C., a natural pH, and a fermentation duration of 84-168 h; an addition of 40-80 g/L glucose is added after 36 h.

Preferably, the fermentation is performed at conditions: an inoculum size of 10%, a shaking speed of 300 rpm, an air flow of 1.39 vvm, a temperature of 26° C., and a natural pH, for 96 h; an addition of 40 g/L glucose is added at 48 h.

As a preference, the mass ratio of the cells to water in step (2) is 1:(0.5-2.5).

Preferably, the mass ratio of the cells to water in step (2) is 1:2.

In the present invention, the cells obtained from the fermentation in step (1) may be dried to give dry algae powders, and the dry algae powders are resuspended in water at a ratio of 1:(2-6).

As a preference, cellulase is added in an amount of 2,000-5,000 U/g, and neutral protease is added in an amount of 2,000-5,000 U/g.

Preferably, cellulase is added in an amount of 2,500 U/g, and neutral protease is added in an amount of 2,500 U/g.

As a preference, the enzymolysis is performed at a temperature of 50-60° C. and a shaking speed of 50-200 r/min for 1.5-6 h.

Preferably, the enzymolysis is performed at a temperature of 55° C. and a shaking speed of 60 r/min for 4 h.

As a preference, the n-hexane is added in an amount of 0.5-4 mL/g by mass of the dry powders of *Schizochytrium* sp.

Preferably, the n-hexane is added in an amount of 2 mL/g by mass of the dry powders of *Schizochytrium* sp.

As a preference, the shaking time for extraction is 1-10 min, the centrifugation is performed at 3,000-8,000 r/min for 3-10 min, and the extraction is repeated for 2-5 times.

Preferably, the shaking time for extraction is 2 min, the centrifugation is performed at 5,000 r/min for 5 min, and the extraction is repeated for 3 times.

As a preference, the concentration under reduced pressure is performed at 35-60° C., and the drying is performed at 40-60° C.

Preferably, the concentration under reduced pressure is performed at 40° C., and the drying is performed at 50° C.

As a preference, the first crystallization is specifically performed by: adding the oil into a crystallization tank, under the protection of nitrogen, stirring and heating the oil to 35-50° C., and maintaining the temperature until the oil is completely melted; gradually cooling the oil to 10° C. within 24 h at a cooling rate of 2-3° C.\h; and maintaining the temperature at 10° C. for more than 6 h.

Preferably, the first crystallization is specifically performed by: adding the oil into a crystallization tank, under the protection of nitrogen, stirring and heating the oil to 40° C., and maintaining the temperature until the oil is completely melted.

As a preference, the second crystallization is specifically performed by: stirring and heating the oil to 20° C., maintaining the temperature until the oil is completely melted, and then gradually cooling to −2° C. within 24 h at a cooling rate of 2° C./h.

As a preference, the deacidification is performed by: under the protection of nitrogen, heating the oil in a water bath to 50-80° C. and maintaining the temperature; slowly adding a sodium hydroxide solution at a mass fraction of 8-12% with stirring, wherein the addition amount of the sodium hydroxide solution is capable of completely neutralizing free fatty acids in the oil; after stirring for 9-13 min, allowing the resultant stand for layer separation, and recovering the upper oil phase to obtain an algae oil after deacidification.

Preferably, the deacidification is performed by: under the protection of nitrogen, heating the oil in a water bath to 60° C. and maintaining the temperature; slowly adding a sodium hydroxide solution at a mass fraction of 10% with stirring, wherein the addition amount of the sodium hydroxide solution is capable of completely neutralizing free fatty acids in the oil; after stirring for 10 min, allowing the resultant stand for layer separation, and recovering the upper oil phase to obtain an algae oil after deacidification.

As a preference, the decolorization is performed by: under the protection of nitrogen, heating the oil in a water bath to 55-70° C. and maintaining the temperature with stirring; gradually increasing the vacuum degree between −0.08 and −0.10 MPa, dehydrating for 12-16 min; adding a decolorant for adsorption for 40-45 min under the constant temperature and vacuum degree with stirring; and conducting vacuum filtration to separate the decolorant.

Preferably, the decolorization is performed by: under the protection of nitrogen, heating the oil in a water bath to 60° C. and maintaining the temperature with stirring; gradually increasing the vacuum degree between −0.09 MPa, dehydrating for 15 min; adding a decolorant for adsorption for 40-45 min under the constant temperature and vacuum degree with stirring; and conducting vacuum filtration to separate the decolorant.

The invention provides a method of producing an oil containing polyunsaturated fatty acids by using *Schizochytrium* sp. The method comprises: performing fermentation using *Schizochytrium* sp.; resuspending the resultant cells after fermentation in water, adding cellulase and neutral protease for enzymolysis; mixing the enzymatic hydrolyzate with n-hexane, shaking, extracting, centrifuging, and collecting the n-hexane phase; concentrating the n-hexane phase under reduced pressure to remove the n-hexane, and drying to obtain an oil; performing a first crystallization and a second crystallization, and then performing cold filtration to obtain a liquid oil after the second crystallization; and subjecting the liquid oil to deacidification and decolorization.

The invention has the following advantages: by regulating fermentation conditions and conducting concentration processing on polyunsaturated fatty acids, the content of eicosapentaenoic acid in the *Schizochytrium* sp. is increased to more than 12%, and the obtained oil is rich in docosahexaenoic acid, docosapentaenoic acid and eicosapentaenoic acid. The invention provides a novel oil product which can be used to replace the polyunsaturated fatty acids from fish oils, showing a great industrial development value.

DETAILED DESCRIPTION OF THE INVENTION

The invention discloses a method of producing a compound polyunsaturated fatty acid oil by using *Schizochytrium* sp. Those skilled in the art may refer to the content of this disclosure and appropriately improve process parameters for implementation. In particular, it should be noted that all similar replacements and modifications will be apparent to those skilled in the art, and those are all considered to be included in the present invention. The methods and applications of the present invention have been described through the preferred examples, and it is obvious that relevant persons may modify or appropriately change and combine the methods and applications described herein without departing from the content, spirit and scope of the present invention in order to realize and apply the technologies of the present invention.

The technical points of the present invention are as follows:

(1) preparing the fermentation medium: glucose 90-120 g/L, sodium glutamate 16-32 g/L, yeast powder 2-16 g/L, magnesium sulfate 1.8-3.24 g/L, ammonium sulfate 3.5-6.8 g/L, KCl 0.5-1.5 g/L, $KH_2PO_4$ 3.2-3.8 g/L, $Na_2SO_4$ 35-45 g/L; performing fermentation at conditions: an inoculum size of 5-15%, a shaking speed of 200-500 rpm, an air flow of 0.5-2 vvm, a temperature of 23-29° C., and a natural pH; adding additional 40-80 g/L of glucose after 36 h;

(2) obtaining wet cells by centrifugation or plate-frame pressure filtration of the fermentation solution of *Schizochytrium* sp., and adding water according to the ratio of algae mud to water 1:0.5-2.5 (if the algae is dried as powders, water is added as a ratio of 1:2-6), then resuspending the *Schizothridium* sp. cells;

(3) adding cellulase and neutral protease at 2,000-5,000 U/g, performing the enzymolysis at 50-60° C. in a water-bathing constant-temperature vibrator at 50-200 r/min for 1.5-6 h;

(4) after the enzymolysis, adding n-hexane at 0.5-4 mL/g by mass of the *Schizochytrium* sp. dry powders, performing shaking for extraction for 1-10 min and centrifuging at 3,000-8,000 r/min for 3-10 min, and collecting the upper n-hexane phase; repeating extraction for 2-5 times and combining the n-hexane phase;

(5) removing the n-hexane by concentrating under reduced pressure (rotary evaporation) at 35-60° C.;

(6) drying the obtained algae oil at 40-60° C. until no weight change, and weighing the obtained oil;

(7) pumping the obtained oil into a crystallization tank with a water jacket system, and adding high-purity nitrogen for protection to prevent oxidation;

(8) stirring and raising the temperature to 35-50° C., and maintaining the temperature until the oil has completely melted;

(9) gradually reducing the temperature by using the water jacket system, and adjusting the temperature reduction rate and the speed reduction rate according to the specific equipment parameters; gradually cooling the oil to 10° C. within 24 h at a cooling rate of 2-3° C.\h, and maintaining the temperature for more than 6 h after the oil temperature has been cooled to 10° C.;

(10) performing cold-filtration on the well-crystallized oil to separate a solid oil and a liquid oil, and subjecting the liquid oil to a second crystallization for fractionation;

(11) performing the second crystallization by: stirring and heating the oil to 20° C., maintaining the temperature until the oil has completely melted, then gradually reducing the temperature by using the water jacket system, the temperature reduction rate and the speed reduction rate are set according to the specific equipment parameters, and gradually cooling the oil to −2° C. within 24 h at a cooling rate of 2° C./h;

(12) performing cold-filtration on the well-crystallized oil to obtain a liquid oil for refining in the next step;

(13) performing deacidification: under the protection of nitrogen, removing free fatty acids using sodium hydroxide solution according to the acid value of the oil at a temperature of 55-65° C., and calculating the addition amount of sodium hydroxide solution according to the amount of free fatty acids; adding the algae oil into a container, charging nitrogen for protection, and heating in a water bath to 50-80° C. and maintaining the temperature constant; slowly adding 8-12% sodium hydroxide solution while stirring, after stirring for 9-13 min, allowing the mixture stand for layer separation, and recovering the upper oil phase to obtain an algae oil after deacidification; and

(14) performing decolorization: using activated clay and activated carbon for decolorization according to the color index of the oil; adding the algae oil into a container, charging nitrogen for protection, and heating in a water bath to 55-70° C. and maintaining the temperature constant and stirring; gradually increasing the vacuum degree to −0.08-− 0.10 MPa, and dehydrating the oil for 12-16 min, then adding a decolorant for adsorption for 40-45 min under the constant temperature, vacuum degree and stirring; removing the decolorant by vacuum filtration to obtain the final product.

The reagents or instruments used in the method provided by the present invention for producing an oil containing polyunsaturated fatty acids by using *Schizochytrium* sp. are all commercially available.

Next, the present invention will be further explained in combination with the examples.

Example 1

This example provides a method of producing an oil containing polyunsaturated fatty acids by using *Schizochytrium* sp.

(1) Fermentation medium (300 L) was prepared: glucose 30 kg, sodium glutamate 6 kg, yeast powder 1.2 kg, magnesium sulfate 0.672 kg, ammonium sulfate 1.44 kg, KCl 0.3 kg, $KH_2PO_4$ 1.05 kg, $Na_2SO_4$ 11.1 kg. Fermentation was performed at conditions: an inoculum size of 10%, a shaking speed of 300 rpm, an air flow of 25 $m^3$/h, a temperature of 26° C., and a natural pH. Additional 12 kg of glucose was added at 48 h at one time.

(2) Wet cells were obtained by centrifugation or plate-frame pressure filtration of the fermentation solution of *Schizochytrium* sp., and water was added according to the weight of algae mud at a ratio of 1:2 (algae mud:water) to resuspend the *Schizothridium* sp. cells.

(3) Cellulase (food grade, 100,000 U/g, Henan Wanbang Industrial Co., Ltd.) and neutral protease (food grade, 200,000 U/g, Henan Wanbang Industrial Co., Ltd.) were added to final concentration of 2,500 U/g at a ratio of 2:8 (U:U). The enzymolysis was performed at 55° C. in a water-bathing constant-temperature vibrator at 60 r/min for 4 h.

(4) After the enzymolysis, n-hexane was added at 2 mL/g according to the dry weight of *Schizochytrium* sp. cells, extraction was performed for 2 min with shaking, and centrifugation was performed at 5000 r/min for 5 min. The upper n-hexane phase was collected. Extraction was repeated for 3 times, and the n-hexane phase was pooled.

(5) The n-hexane was removed by concentrating under reduced pressure (rotary evaporation) at 40° C.

(6) The obtained algae oil was dried at 50° C. to until no weight change, and the oil was weighed.

(7) The obtained oil was pumped into a crystallization tank with a water jacket system, and high-purity nitrogen protection was added to prevent oxidation.

(8) Stirring was performed and the temperature was raised to 40° C., and the temperature was maintained until the oil had completely melted.

(9) The temperature was gradually reduced by using the water jacket system, and the temperature reduction rate and the rotary-speed reduction rate were set according to the specific equipment parameters; the oil was gradually cooled to 10° C. within 24 h at a cooling rate of 2-3° C./h, and the temperature was maintained for more than 6 h after the oil temperature had been cooled to 10° C.

(10) The well-crystallized oil was subjected to cold-filtration to give two phases of a solid oil and a liquid oil, and the liquid oil was subjected to second crystallization.

(11) The second crystallization was performed by: stirring and heating the oil to 20° C., maintaining the temperature until the oil had completely melted, then gradually reducing the temperature by using the water jacket system, setting the temperature reduction rate and the rotary-speed reduction rate according to the specific equipment parameters, and gradually cooling the oil to −2° C. within 24 h at a cooling rate of 2° C./h.

(12) The well-crystallized oil was subjected to cold-filtration to give a liquid oil for refining in the next step;

(13) The oil was subjected to deacidification, free fatty acids were removed under the protection of nitrogen using sodium hydroxide solution according to the acid value of the oil, the deacidification temperature was 60° C., and the addition amount of sodium hydroxide solution was calculated according to the amount of free fatty acids; the algae oil was added into a container, nitrogen was charged for protection, and heating was performed in a water bath to 60° C. and the temperature was maintained constant; a 10% sodium hydroxide solution was slowly added while stirring, after stirring for 10 min, the solution was left stand for layer separation, and the upper oil phase was recovered to obtain an algae oil after deacidification.

(14) The oil was subjected to decolorization, decolorization was performed using activated clay and activated carbon according to the color index of the oil; algae oil was added to a container, nitrogen was charged for protection, and heating was performed in a water bath to 60° C. and a constant temperature and stirring were maintained; the vacuum degree was gradually increased to −0.09 MPa, and the material was dehydrated for 15 min, then a decolorant was added for adsorption for 40-45 min under the constant temperature, vacuum degree and stirring. The decolorant was removed by vacuum filtration to obtain the final product.

Using a 500 L fermentation tank (with a fermentation volume of 300 L), after 4 days of fermentation, 40.82 kg of glucose was consumed, and 13.80 kg of dry algae powders were obtained with an oil content of 36.60%. After the cells were broken, 5.05 kg of oil from *Schizochytrium* sp. was obtained, containing DHA 27.67%, ω6DPA 11.02%, w3 DPA 1.87%, and EPA 9.44%. The PUFA contents of the final product liquid oil after concentration processing were EPA 21.14%, DHA 36.96%, ω3 DPA 2.38%, and w6 DPA 8.23%. The PUFA content, especially the EPA content, in the oil prepared from *Schizochytrium* sp. according to this example is more than 10 times the EPA content in the literatures. Thus the invention has great innovation and industrial development value.

The PUFAs content, especially the EPA content, in the oil prepared from *Schizochytrium* sp. according to this example is more than 10 times the EPA content in the disclosed literatures, and at the same time it contains a higher content of DPA. DHA, EPA and DPA, which are rich in this oil, have a good effect in helping to lower blood lipids and preventing and reducing the risk of cardiovascular disease. At the same time, the production process is stable and has very high feasibility of large-scale production and industrialization. Therefore, the invention has great innovation and industrial development value in terms of process and use.

The above is only a preferred example of the present invention. It should be noted that for those ordinary skilled in the art, several improvements and retouches may be made without departing from the principles of the present invention. These improvements and retouches should also be regarded to be within the protection scope of the present invention.

What is claimed is:

1. A method of producing an oil containing polyunsaturated fatty acids by using *Schizochytrium* sp., comprising the following steps:
   Step (1): performing fermentation using *schizochytrium* sp., wherein the medium for fermentation comprises glucose 90-120 g/L, sodium glutamate 16-32 g/L, yeast powder 2-16 g/L, magnesium sulfate 1.8-3.24 g/L, ammonium sulfate 3.5-6.8 g/L, potassium chloride 0.5-1.5 g/L, potassium dihydrogen phosphate 3.2-3.8 g/L, sodium sulfate 35-45 g/L, and water as balance;
   Step (2): resuspending the resultant cells after fermentation in water, adding cellulase and neutral protease for enzymolysis to obtain an enzymatic hydrolyzate;
   Step (3): mixing the enzymatic hydrolyzate with n-hexane, shaking, extracting, centrifuging, and collecting the n-hexane phase; concentrating the n-hexane phase under reduced pressure to remove the n-hexane, and drying to obtain an oil;
   Step (4): performing a first crystallization on the oil, then performing cold filtration to obtain a solid oil and a liquid oil;
   Step (5): performing a second crystallization on the liquid oil, then performing cold filtration to obtain a liquid oil after the second crystallization; and
   Step (6): subjecting the liquid oil after the second crystallization to deacidification and decolorization.

2. The method according to claim 1, wherein the fermentation is performed at conditions: an inoculum size of 5-15%, a shaking speed of 200-500 rpm, an air flow of 0.5-2 vvm, a temperature of 23-29° C., a natural pH, and a fermentation duration of 84-168 h; an addition of 40-80 g/L glucose is added after 36 h.

3. The method according to claim 1, wherein a mass ratio of the cells to the water in Step (2) is 1:(0.5-2.5).

4. The method according to claim 1, wherein the cellulase is added at an amount of 2,000-5,000 U/g, and the neutral protease is added at an amount of 2,000-5,000 U/g.

5. The method according to claim 1, wherein the enzymolysis is performed at a temperature of 50-60° C. for 1.5-6 h with a shaking speed of 50-200 r/min.

6. The method according to claim 1, wherein the n-hexane is added at an amount of 0.5-4 mL/g by mass of dry powder of *Schizochytrium* sp.;
   the shaking time for extraction is 1-10 min, the centrifugation is performed at 3,000-8,000 r/min for 3-10 min, and the extraction is repeated for 2-5 times; and
   the concentration under reduced pressure is performed at 35-60° C., and the drying is performed at 40-60° C.

7. The method according to claim 1, wherein the first crystallization is specifically performed by: adding the oil into a crystallization tank, under the protection of nitrogen, stirring and heating the oil to 35-50° C., and maintaining the temperature until the oil is completely melted; gradually cooling the oil to 10° C. within 24 h at a cooling rate of 2-3° C./h; and maintaining the temperature at 10° C. for more than 6 h.

8. The method according to claim 1, wherein the second crystallization is specifically performed by: stirring and heating the oil to 20° C., maintaining the temperature until the oil is completely melted, and then gradually cooling to −2° C. within 24 h at a cooling rate of 2° C./h.

9. The method according to claim 1, wherein the deacidification is performed by: under the protection of nitrogen, heating the oil in a water bath to 50-80° C. and maintaining the temperature; slowly adding a sodium hydroxide solution at a mass fraction of 8-12% with stirring, wherein the addition amount of the sodium hydroxide solution is capable of completely neutralizing free fatty acids in the oil; after stirring for 9-13 min, allowing the resultant stand for layer separation, and recovering the upper oil phase to obtain an algae oil after deacidification.

10. The method according to claim 1, wherein the decolorization is performed by: under the protection of nitrogen, heating the oil in a water bath to 55-70° C. and maintaining the temperature with stirring; gradually increasing the vacuum degree between −0.08 and −0.10 MPa, dehydrating for 12-16 min; adding a decolorant for adsorption for 40-45 min under the constant temperature and vacuum degree with stirring; and conducting vacuum filtration to separate the decolorant.

* * * * *